US012664632B2

(12) United States Patent
Kanamori et al.

(10) Patent No.: US 12,664,632 B2
(45) Date of Patent: Jun. 23, 2026

(54) IMAGE PROCESSING APPARATUS, RADIATION DETECTOR, AND RECORDING MEDIUM

(71) Applicant: Konica Minolta, Inc., Tokyo (JP)

(72) Inventors: Koutarou Kanamori, Hachioji (JP); Ryo Higashide, Ichinomiya (JP)

(73) Assignee: KONICA MINOLTA, INC., Tokyo (JP)

( * ) Notice: Subject to any disclaimer, the term of this patent is extended or adjusted under 35 U.S.C. 154(b) by 368 days.

(21) Appl. No.: 18/310,845

(22) Filed: May 2, 2023

(65) Prior Publication Data

US 2023/0368358 A1 Nov. 16, 2023

(30) Foreign Application Priority Data

May 10, 2022 (JP) ................................ 2022-077336
Apr. 14, 2023 (JP) ................................ 2023-066299

(51) Int. Cl.

| | |
|---|---|
| ***G06V 40/16*** | (2022.01) |
| ***A61B 6/42*** | (2024.01) |
| ***G06T 5/20*** | (2006.01) |
| ***G06T 5/40*** | (2006.01) |
| ***G06T 7/00*** | (2017.01) |

(52) U.S. Cl.

CPC .......... *G06T 7/0002* (2013.01); *A61B 6/4208* (2013.01); *G06T 5/20* (2013.01); *G06T 5/40* (2013.01); *G06T 2207/10116* (2013.01); *G06T 2207/10144* (2013.01); *G06T 2207/30168* (2013.01)

(58) Field of Classification Search

CPC .......... G06T 7/0002; G06T 5/20; G06T 5/40; G06T 2207/10116; G06T 2207/10144; G06T 2207/30168; A61B 6/4208; A61B 6/545; A61B 6/542

See application file for complete search history.

(56) References Cited

U.S. PATENT DOCUMENTS

2012/0300904 A1* 11/2012 Shimada ................ A61B 6/463 378/62
2016/0302752 A1* 10/2016 Ito ............................ G06T 5/40
2020/0273165 A1* 8/2020 Kanamori ............. G06T 7/0012

FOREIGN PATENT DOCUMENTS

JP 2019-058608 A 4/2019
JP 2020-130796 A 8/2020

* cited by examiner

*Primary Examiner* — Amandeep Saini
*Assistant Examiner* — Mehrazul Islam
(74) *Attorney, Agent, or Firm* — LUCAS & MERCANTI, LLP

(57) ABSTRACT

An image processing apparatus includes a first hardware processor that calculates an exposure index related to noise of a radiographic image based on image data of the radiographic image. The first hardware processor creates a density histogram of a region of interest set in the entire radiographic image or a part of the radiographic image, extracts a plurality of pixels having signal values within a specific range from the created density histogram, analyzes variations in the signal values of the plurality of extracted pixels, and calculates the exposure index based on an analysis result of the variations.

14 Claims, 11 Drawing Sheets

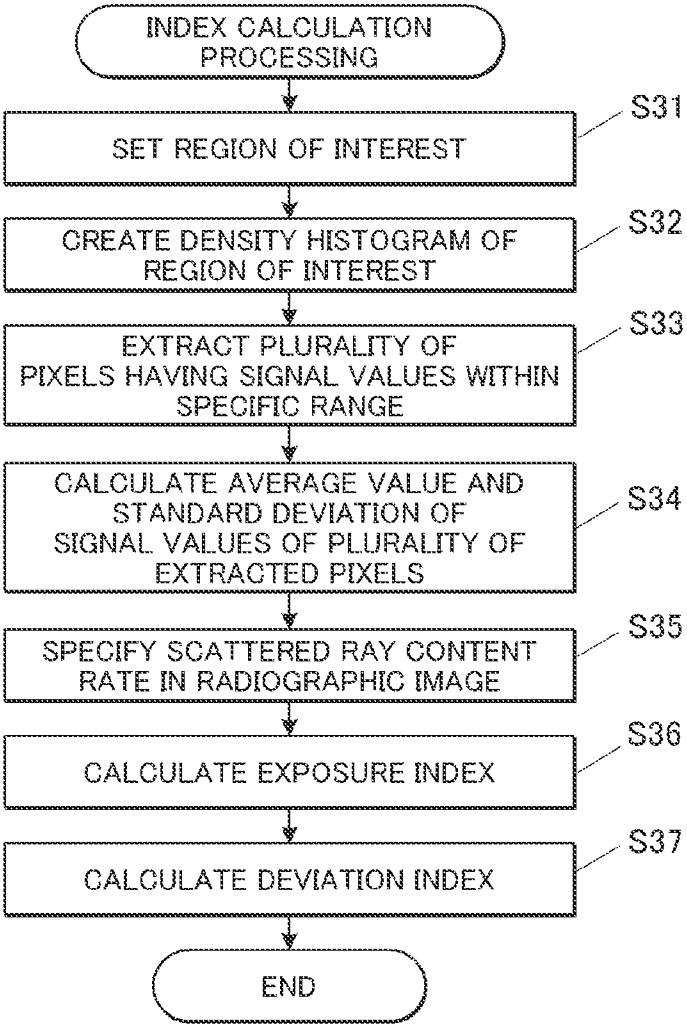

FIG.5

INDEX CALCULATION
PROCESSING

SET REGION OF INTEREST — S31

CREATE DENSITY HISTOGRAM OF
REGION OF INTEREST — S32

EXTRACT PLURALITY OF
PIXELS HAVING SIGNAL VALUES WITHIN
SPECIFIC RANGE — S33

CALCULATE AVERAGE VALUE AND
STANDARD DEVIATION OF
SIGNAL VALUES OF PLURALITY OF
EXTRACTED PIXELS — S34

SPECIFY SCATTERED RAY CONTENT
RATE IN RADIOGRAPHIC IMAGE — S35

CALCULATE EXPOSURE INDEX — S36

CALCULATE DEVIATION INDEX — S37

END

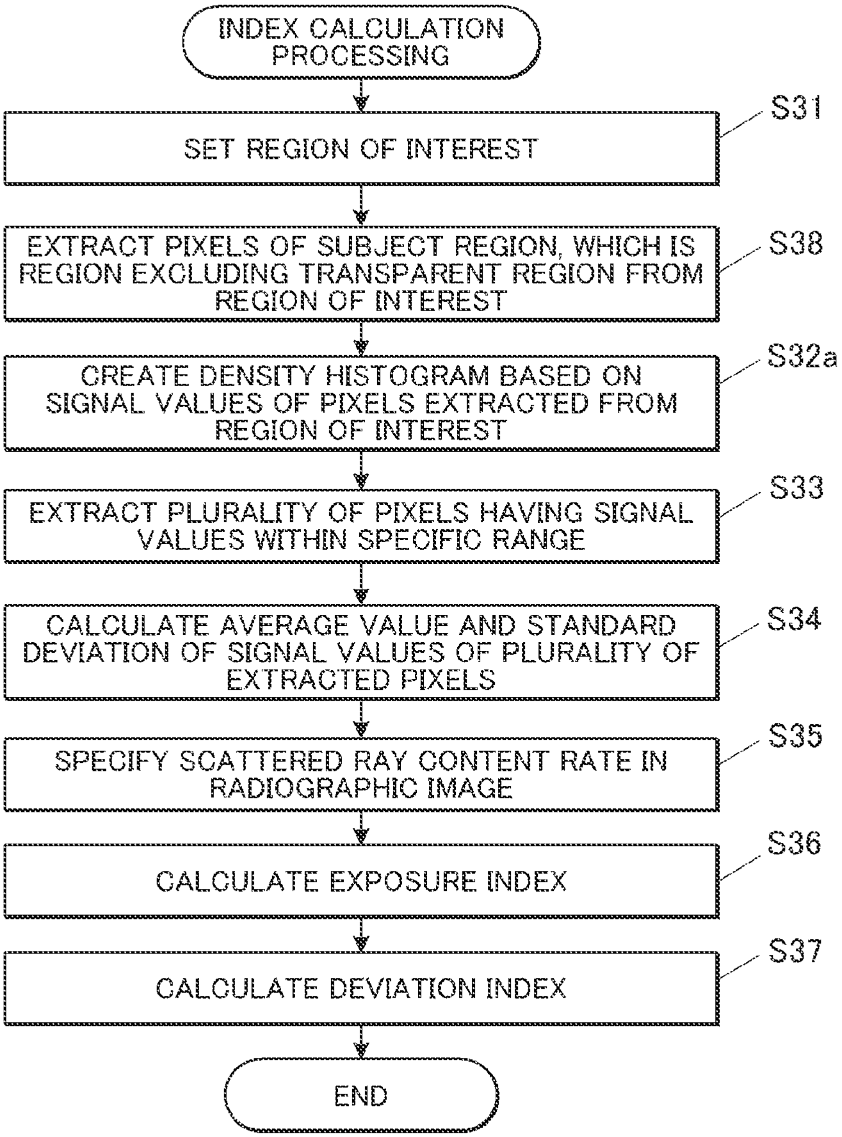

FIG.13

INDEX CALCULATION
PROCESSING

SET REGION OF INTEREST — S31

EXTRACT PIXELS OF SUBJECT REGION, WHICH IS
REGION EXCLUDING TRANSPARENT REGION FROM
REGION OF INTEREST — S38

CREATE DENSITY HISTOGRAM BASED ON
SIGNAL VALUES OF PIXELS EXTRACTED FROM
REGION OF INTEREST — S32a

EXTRACT PLURALITY OF PIXELS HAVING SIGNAL
VALUES WITHIN SPECIFIC RANGE — S33

CALCULATE AVERAGE VALUE AND STANDARD
DEVIATION OF SIGNAL VALUES OF PLURALITY OF
EXTRACTED PIXELS — S34

SPECIFY SCATTERED RAY CONTENT RATE IN
RADIOGRAPHIC IMAGE — S35

CALCULATE EXPOSURE INDEX — S36

CALCULATE DEVIATION INDEX — S37

END

IMAGE PROCESSING APPARATUS, RADIATION DETECTOR, AND RECORDING MEDIUM

CROSS-REFERENCE TO RELATED APPLICATIONS

The entire disclosures of Japanese Patent Application No. 2022-077336 filed on May 10, 2022 and Japanese Patent Application No. 2023-066299 filed on Apr. 14, 2023 are incorporated herein by reference in its entirety.

TECHNICAL FIELD

The present invention relates to an image processing apparatus, a radiation detector, and a recording medium.

DESCRIPTION OF THE RELATED ART

Conventionally, a radiographic imaging system is known that detects radiation emitted to a subject by using a radiation detector and captures a radiographic image. In recent years, in the radiographic imaging system, imaging conditions such as radiation intensity are managed based on the unified index (exposure index; hereinafter, referred to as "EI") related to the dose of radiation reaching the radiation detector.

In the EI, however, how much scattered rays diffusely reflected by a part of a subject are included in the radiation reaching the radiation detector is not taken into consideration. For this reason, even if the imaging conditions are adjusted such that the EI becomes an appropriate value, there are cases where a radiographic image with a desired image quality cannot be obtained due to a large amount of noise depending on the scattered ray content rate.

On the other hand, a technique in which the magnitude of noise is evaluated by performing a spatial frequency analysis on a generated radiographic image and an exposure index related to noise (for example, an index that is a value corresponding to the signal-to-noise ratio (SN ratio)) is calculated and used to manage imaging conditions has been proposed in JP 2019-58608 A and JP 2020-130796 A. By adjusting the imaging conditions such that the exposure index becomes an appropriate value, a radiographic image with a desired image quality and reduced noise can be obtained.

SUMMARY OF THE INVENTION

However, since the calculation of the exposure index requires spatial frequency analysis including Fourier transform processing, the computational load is heavy. Therefore, there is a problem that a large-scale apparatus with high computing power is required or it takes time to calculate the exposure index. For this reason, there has been a demand for an exposure index that can be calculated by simpler processing.

It is an object of the present invention to provide an image processing apparatus, a radiation detector, and a program capable of calculating an appropriate exposure index with simpler processing.

In order to achieve the aforementioned object, according to one aspect of the present invention, there is provided an image processing apparatus including a first hardware processor that calculates an exposure index related to noise of a radiographic image based on image data of the radiographic image. The first hardware processor creates a density histogram of a region of interest set in the entire radiographic image or a part of the radiographic image, extracts a plurality of pixels having signal values within a specific range from the created density histogram, analyzes variations in the signal values of the plurality of extracted pixels, and calculates the exposure index based on an analysis result of the variations.

In order to achieve the aforementioned object, according to another aspect of the present invention, there is provided a radiation detector including the image processing apparatus according to the one aspect of the present invention, a detection sensor that detects radiation and performs conversion into an electrical signal, and a second hardware processor that generates the image data of the radiographic image based on a signal value of the electrical signal output from the detection sensor.

In order to achieve the aforementioned object, according to still another aspect of the present invention, there is provided a non-transitory recording medium storing a computer readable program causing a computer to execute calculating an exposure index related to noise of a radiographic image based on image data of the radiographic image. In the calculation, a density histogram of a region of interest set in the entire radiographic image or a part of the radiographic image is created, a plurality of pixels having signal values within a specific range are extracted from the created density histogram, variations in the signal values of the plurality of extracted pixels are analyzed, and the exposure index is calculated based on an analysis result of the variations.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 5 is a flowchart showing the control procedure of index calculation processing;

FIG. 13 is a flowchart showing the control procedure of index calculation processing according to a fourth modification example.

DETAILED DESCRIPTION

Hereinafter, an image processing apparatus, a radiation detector, and a program according to embodiments of the present invention will be described with reference to the diagrams.

Configuration of Radiographic Imaging System

Figure 1:
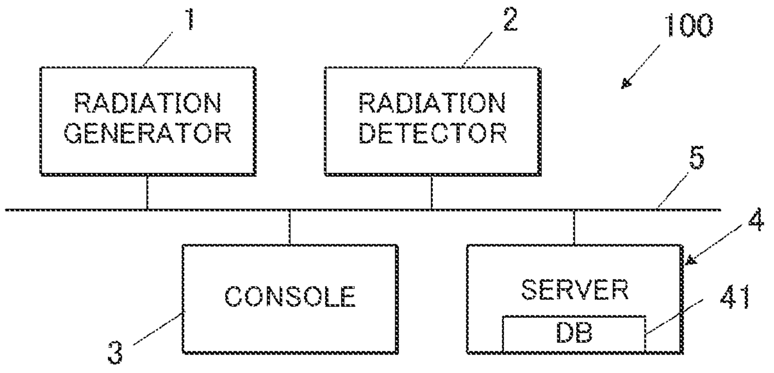
FIG. 1 is a block diagram showing the configuration of a radiographic imaging system.

FIG. 1 is a block diagram showing the configuration of a radiographic imaging system 100.

The radiographic imaging system 100 according to the present embodiment includes a radiation generator 1, a radiation detector 2, a console (image processing apparatus) 3, and a server 4. These can communicate with each other through a communication network 5 (for example, a LAN (local area network), a WAN (wide area network), or the Internet).

The radiographic imaging system 100 may be connectable to a hospital information system (HIS), a radiology information system (RIS), a picture archiving and communication system (PACS), an image analyzer, and the like that are not shown.

Although not shown, the radiation generator 1 includes a generator that applies a voltage according to preset irradiation conditions based on an operation on an irradiation instruction switch, a radiation source that generates a dose of radiation (for example, X-rays) corresponding to the voltage applied from the generator, and the like. The irradiation conditions include set values, such as a tube voltage (kV), a tube current (mA), and a tube current-time product (mAs) of the radiation source. Among these, the tube current-time product is a product of the tube current and the irradiation time (sec).

The radiation generator 1 generates radiation (for example, X-rays) corresponding to a radiographic image to be captured (still image and moving image).

The radiation generator 1 may be installed in the imaging room, or may be configured so as to be movable by being mounted on a medical care vehicle or the like together with the console 3 and the like.

The radiation detector 2 detects radiation emitted from the radiation generator 1 and generates a radiographic image reflecting the two-dimensional distribution of the dose of the detected radiation. By emitting the radiation from the radiation generator 1 to a subject, such as a patient, in a state in which the subject is placed between the radiation generator 1 and the radiation detector 2, a radiographic image reflecting the internal structure or state of the subject can be obtained. The radiation detector 2 may be of a dedicated machine type integrated with an imaging table or may be of a portable type (cassette type).

Figure 2:
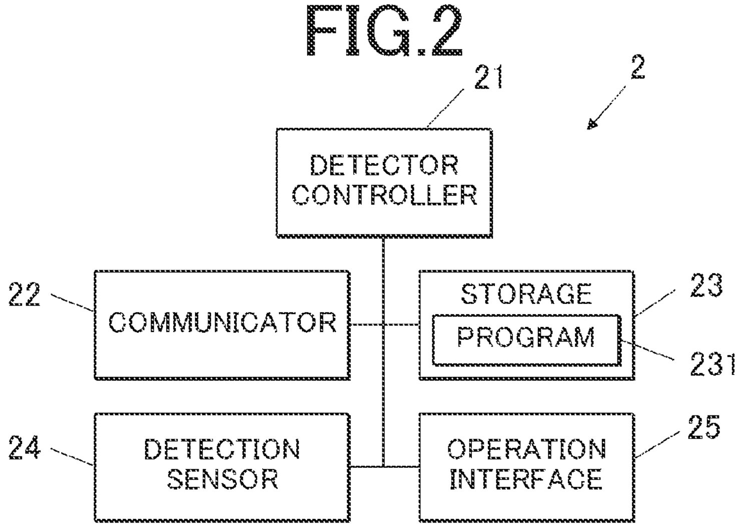
FIG. 2 is a block diagram showing the main functional configuration of a radiation detector.

FIG. 2 is a block diagram showing the main functional configuration of the radiation detector 2.

The radiation detector 2 includes a detector controller 21, a communicator 22, a storage 23, a detection sensor 24, an operation interface 25, and the like, and these are connected to each other through a bus.

The detector controller 21 is a hardware processor (second hardware processor) having a CPU (central processing unit), a RAM (random access memory), and the like. The CPU of the detector controller 21 reads out a program 231 stored in the storage 23 and loads the program 231 to the RAM, and executes various processes according to the loaded program 231. The detector controller 21 controls the operation of each unit of the radiation detector 2 by executing various processes according to the program 231 by the CPU. The detector controller 21 functions as an image data generator that generates image data of a radiographic image based on the signal value (pixel value) of an electrical signal output from the detection sensor 24 by executing various processes according to the program 231 by the CPU.

The communicator 22 is a communication module or the like. The communicator 22 transmits and receives various signals or various kinds of data to and from another device or the like connected through the communication network 5.

The storage 23 is a non-transitory recording medium readable by the detector controller 21 as a computer, and stores the program 231 described above and various kinds of data, such as parameters necessary for executing the program 231. The program 231 is stored in the storage 23 in the form of computer-readable program code. The storage 23 is a non-volatile semiconductor memory or the like. The storage 23 temporarily stores the radiographic image generated by the detector controller 21.

The detection sensor 24 detects the radiation emitted from the radiation generator 1, converts the radiation into an electrical signal, and outputs the electrical signal. Specifically, the detection sensor 24 includes: a substrate on which pixels are arranged in a two-dimensional (matrix) pattern, each of which includes a radiation detection element that generates an electric charge corresponding to the radiation dose when receiving radiation and a switching element that accumulates and discharges the electric charge; a scanning circuit for switching ON/OFF of each switching element; and a read circuit for reading and outputting the amount of electric charge emitted from each pixel as a signal value of an electrical signal. The detection sensor 24 may have a built-in scintillator or the like, so that the emitted radiation is converted into light having another wavelength, such as visible light, by the scintillator and an electric charge corresponding to the converted light is generated (so-called indirect type), or may directly generate an electric charge from the radiation without a scintillator or the like (so-called direct type).

The detector controller 21 generates a radiographic image based on the signal value of the electrical signal output from the detection sensor 24 and stores the radiographic image in the storage 23. The detector controller 21 transmits the radiographic image to an external device (console 3 or the like) through the communicator 22. The detector controller 21 causes the detection sensor 24 to detect radiation and output an electrical signal in synchronization with the timing at which radiation is emitted from the radiation generator 1, thereby generating a radiographic image corresponding to the emitted radiation.

The operation interface 25 is formed by physical buttons and the like exposed on the surface of the housing of the radiation detector 2. The operation interface 25 outputs a control signal corresponding to the operation performed by the user to the detector controller 21.

The console 3 shown in FIG. 1 can determine radiographic imaging conditions (including the irradiation conditions described above; for example, tube voltage, tube current, irradiation time, tube current-time product, frame rate, physique of the subject, and the presence or absence of a grid) of the radiographic imaging system 100 based on imaging order information obtained from other systems (HIS, RIS, and the like) and a user operation and set the radiographic imaging conditions in the radiation generator 1, the radiation detector 2, and the like. The console 3 acquires image data of the radiographic image from the radiation detector 2, and performs predetermined image processing on the image data of the radiographic image or displays the radiographic image on a display device.

Figure 3:
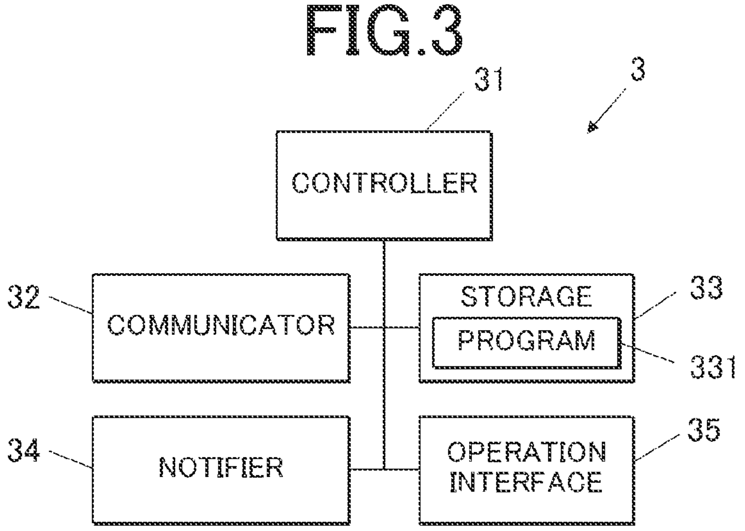
FIG. 3 is a block diagram showing the main functional configuration of a console.

FIG. 3 is a block diagram showing the main functional configuration of the console 3.

The console 3 includes a controller 31, a communicator 32, a storage 33, a notifier 34, an operation interface 35, and the like, and these are connected to each other through a bus.

The controller 31 is a hardware processor having a CPU, a RAM, and the like. The CPU of the controller 31 reads out a program 331 stored in the storage 33 and loads the program 331 to the RAM, and executes various processes according to the loaded program 331. The controller 31 controls the operation of each unit of the console 3 by causing the CPU to execute various processes according to the program 331. The controller 31 (first hardware processor) functions as a calculator, an image processor, a determinator, and the like by executing various processes according to the program 331 by the CPU. The calculator calculates an exposure index (first exposure index) related to noise in the radiographic image based on the image data of the radiographic image. The image processor performs predetermined image processing on the image data of the radiographic image. The determinator determines radiographic imaging conditions in the radiographic imaging system 100 based on the exposure index.

The communicator 32 is a communication module or the like. The communicator 32 transmits and receives various signals or various kinds of data to and from another device or the like connected through the communication network 5.

The storage 33 is a non-transitory recording medium readable by the controller 31 as a computer, and stores the program 331 described above and various kinds of data, such as parameters necessary for executing the program 331. The program 331 is stored in the storage 33 in the form of computer-readable program code. The storage 33 includes a non-volatile semiconductor memory, a hard disk, or the like.

The storage 33 stores a plurality of target values of the exposure index for each imaging part and imaging conditions (for example, at least one of the physique (normal, fat, thin, and the like) of the subject, the presence or absence of a grid, the presence or absence of scattered ray correction processing, and the like). The exposure index and the target value of the exposure index will be described later.

The storage 33 may be capable of storing a radiographic image.

The notifier 34 is a display device such as an LCD (liquid crystal display) or a CRT (cathode ray tube) that displays an image, a lamp that emits light (such as an LED), a speaker that outputs sound, a vibrator that vibrates, and the like. The notifier 34 performs notification related to various indices, which will be described later, based on a control signal input from the controller 31 or power supplied from a power supply circuit (not shown) controlled by the controller 31.

The operation interface 35 is formed by a keyboard including cursor keys, number input keys, and various function keys, a pointing device such as a mouse, a touch panel laminated on the surface of the display device, and the like. The operation interface 35 outputs a control signal corresponding to the operation performed by the user to the controller 31.

The server 4 shown in FIG. 1 is a PC, a dedicated device, a virtual server on the cloud, or the like. The server 4 has a database 41. In the present embodiment, the database 41 is provided in the server 4 independent of the console 3 and the like. However, the database 41 may be provided in the console 3 or may be provided in another device provided in the radiographic imaging system 100. In addition, when another system such as a PACS is connected to the radiographic imaging system 100, the database 41 may be provided in another system.

In the radiographic imaging system 100 according to the present embodiment configured as described above, the radiation source of the radiation generator 1 and the radiation detector 2 are arranged so as to face each other with a gap therebetween and the radiation from the radiation source is emitted to the subject placed between the radiation source of the radiation generator 1 and the radiation detector 2, so that it is possible to capture a radiographic image of the subject.

When the radiographic image is set to be captured as a static image, emission of radiation and generation of a radiographic image are performed only once per imaging operation (pressing the irradiation instruction switch). When the radiographic image is set to be captured as a moving image, emission of pulsed radiation and generation of a frame image are repeated a plurality of times in a short time (for example, 15 times per second) for each imaging operation.

Configuration of Radiographic Imaging System

Next, the operation of the radiographic imaging system 100 will be described focusing on the operation of calculating the exposure index.

In the radiographic imaging system 100 according to the present embodiment, when capturing a radiographic image, an exposure index is calculated based on the image data of the captured radiographic image. This exposure index is related to noise, unlike the conventionally used EI (hereinafter, also referred to as "second exposure index"). Specifically, the exposure index of the present embodiment is a value corresponding to the ratio of the magnitude of a signal to the magnitude of noise (SN ratio) in the radiographic image. As for the signal amount, a value obtained by subtracting the scattered ray, which is the cause of a reduction in contrast, from the radiation reaching the radiation detector 2 is used. The amount of scattered rays is calculated based on the scattered ray content rate estimated from the body thickness. As described above, the exposure index of the present embodiment is an index related to noise in a radiographic image obtained as a result of radiation exposure. In addition, the exposure index of the present embodiment is a numerical value that varies depending, simply, not only on the amount of radiation reaching the radiation detector 2 but also on the magnitude of noise or the scattered ray content rate of radiation that affects image quality.

For the exposure index, a target value is set in advance. The target value of the exposure index is a numerical value that is desirably reached by the exposure index calculated after imaging. The target value of the exposure index is determined in advance in association with a combination of an imaging part of a subject, imaging conditions of a radiographic image, and the like and is stored in the storage 33. The target value of the exposure index may be stored in the database 41. When capturing a radiographic image, a target value corresponding to the combination of an imaging part and imaging conditions in the imaging is selected and set.

The image quality of a radiographic image can be evaluated according to how much the exposure index calculated based on the image data of the radiographic image deviates from the target value set in advance. In the following description, first, a case where the user is notified of the calculated exposure index to prompt the user to adjust the imaging conditions will be described as an example. Other uses of the exposure index will be exemplified in first and second modification examples, which will be described later.

Hereinafter, processing at the time of imaging executed by the controller 31 of the console 3 when capturing a radiographic image will be described with reference to a flowchart.

Figure 4:
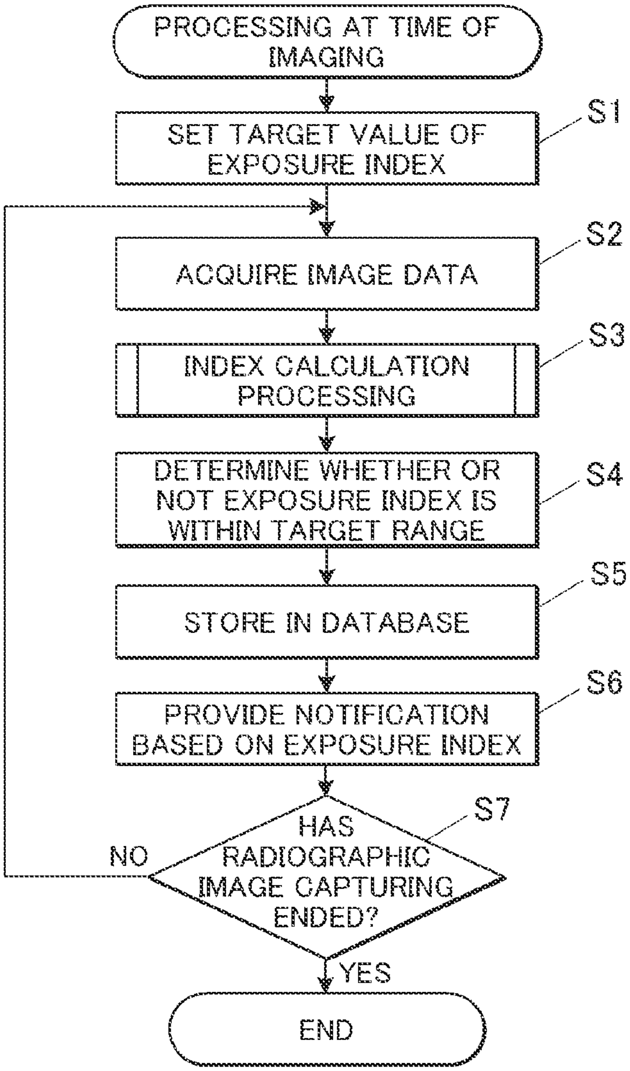
FIG. 4 is a flowchart showing the control procedure of processing at the time of imaging.

FIG. 4 is a flowchart showing the control procedure of the processing at the time of imaging The processing at the time of imaging is started, for example, when the user performs a predetermined imaging start operation.

When the processing at the time of imaging is started, the controller 31 sets the target value of the exposure index (step S1). The controller 31 acquires the imaging part of the subject and the imaging conditions at that time, and selects and sets a target value corresponding to the combination of the imaging part and the imaging conditions from the plurality of target values stored in the storage 33.

After the target value is set, a radiographic image is captured by the radiation generator 1 and the radiation detector 2. During the time, the controller 31 of the console 3 is on standby.

The processing of step S1 may be executed as independent processing different from the processing at the time of imaging, and the processing of step S2 or step S3, which will be described later, may be executed when a predetermined start operation is performed or when the image data of a radiographic image is acquired.

When imaging is performed, the controller 31 acquires the image data of the radiographic image (step S2). The controller 31 acquires the image data of the radiographic image from the radiation detector 2. However, without being limited to this, the controller 31 may receive or acquire the image data of the radiographic image from a device other than the radiation detector 2 or from a storage medium. When the storage 33 of the console 3 is configured to be able to store image data, the image data stored in the storage 33 after being received or acquired from another device may be read.

The controller 31 executes index calculation processing for calculating an exposure index related to noise in the radiographic image based on the acquired image data (step S3). The image data used in the index calculation processing may be either image data before performing logarithmic conversion of the value of radiation detected by the detection sensor 24 of the radiation detector 2 or image data after performing the logarithmic conversion.

FIG. 5 is a flowchart showing the control procedure of the index calculation processing.

When the index calculation processing is called, the controller 31 sets a region of interest (ROI) in the entire radiographic image or in a part of the radiographic image (step S31). The region of interest ROI may be automatically set by the controller 31 based on the result of predetermined image recognition processing on a radiographic image Im, set imaging order information, or the like. The region of interest ROI may be set based on the operation performed by the user on the operation interface 35 (that is, the user may be able to manually set the region of interest ROI). If the user can manually set the region of interest ROI, a region desired by the user can be set as the region of interest ROI.

Figure 6:
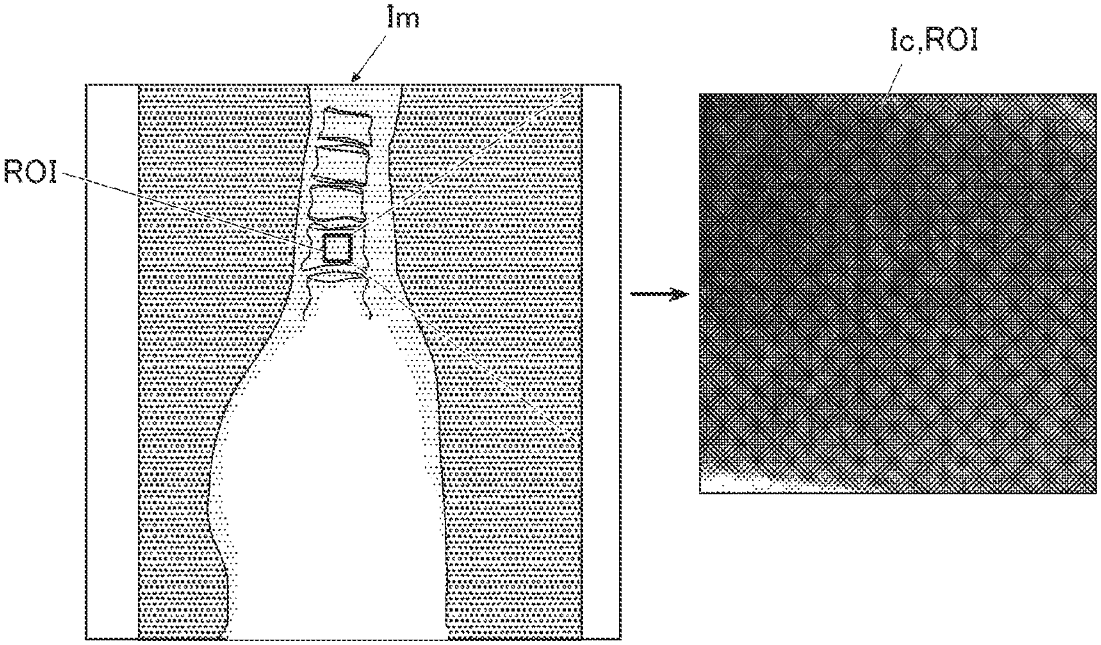
FIG. 6 is a diagram illustrating a method of setting a region of interest in the index calculation processing.
Figure 8A:
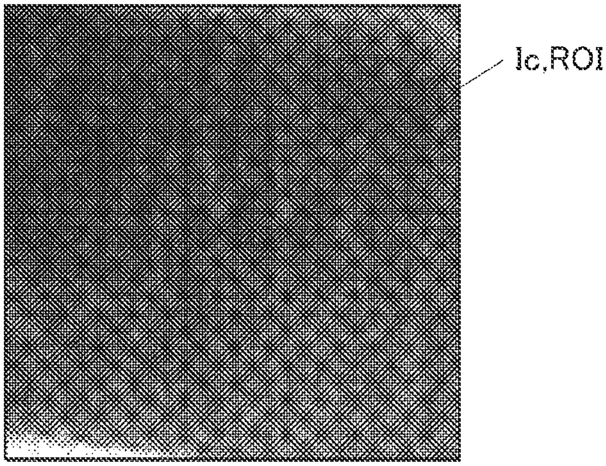
FIG. 8A is a diagram showing an example of a cut image corresponding to a region of interest.

After the region of interest ROI is set, for example, as shown on the right side in FIG. 6 and FIG. 8A, the region of interest ROI may be extracted from the radiographic image Im and handled as a cut image Ic different from the radiographic image Im.

Figure 7:
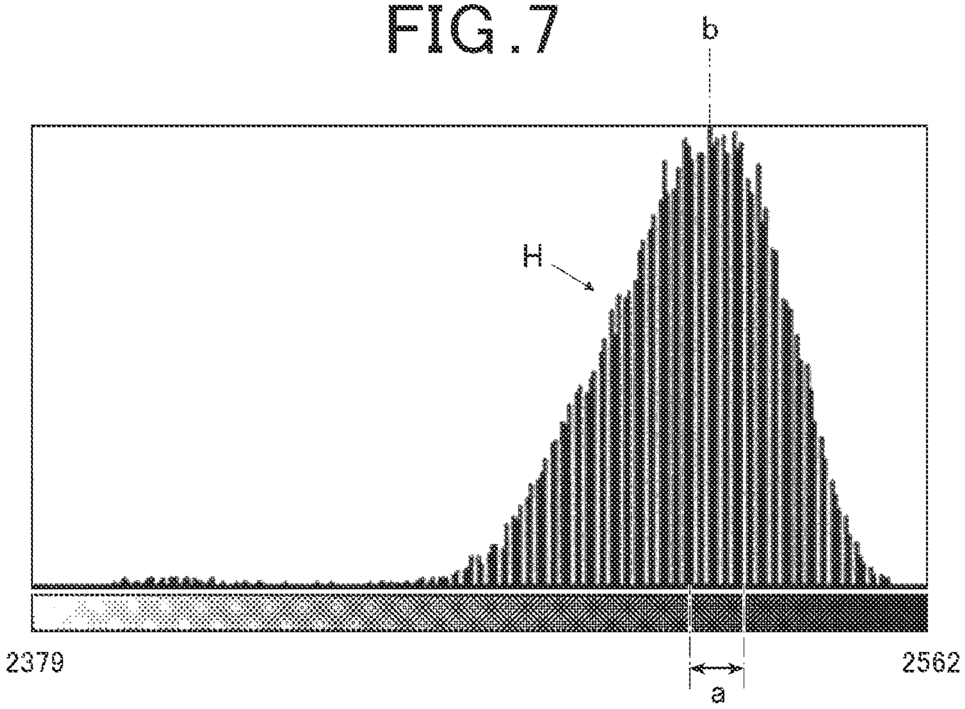
FIG. 7 is a diagram showing an example of a density histogram.

The controller 31 creates a density histogram H of the set region of interest ROI (step S32 in FIG. 5). FIG. 7 is a diagram showing an example of the density histogram H. In the density histogram H shown in FIG. 7, the horizontal axis indicates a signal value indicating the density in the image data of the radiographic image, and the vertical axis indicates the number of pixels having each signal value. In the example shown in FIG. 7, the minimum value of the signal value is "2379" and the maximum value is "2562", and the distribution is set such that the number of pixels having signal values between the minimum value and the maximum value is maximized.

Figure 8B:
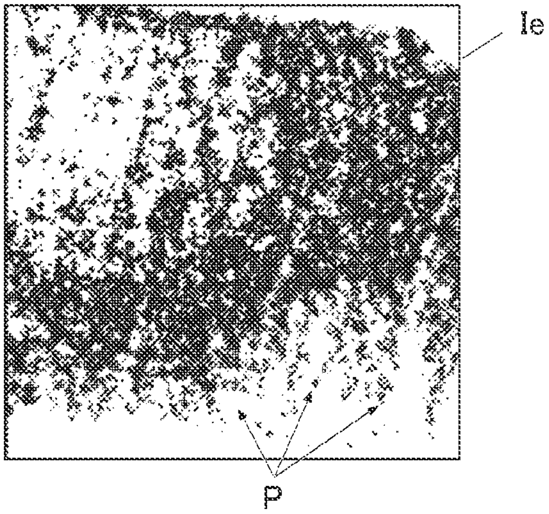
FIG. 8B is a diagram showing an example of an extracted image including a plurality of pixels extracted from the region of interest.

The controller 31 extracts a plurality of pixels having signal values within a specific range a from the created density histogram H (step S33 in FIG. 5). A pixel having a signal value within the specific range a is hereinafter referred to as a "pixel P". The specific range a can be a range within a predetermined width centered on the representative value of the signal values in the density histogram H. For example, when the representative value of the signal values is "b", "b±c %" may be set as the specific range a. That is, the lower limit of the specific range a may be "b×(100−c)/100" and the upper limit may be "b×(100+c)/100". For example, when the value c is "5(%)", the lower limit of the specific range a is "0.95b" and the upper limit is "1.05b". FIG. 8B shows an extracted image Ie obtained by leaving a plurality of pixels P extracted in step S33 as they are and whitening pixels that are not extracted in the cut image Ic (region of interest ROI) shown in FIG. 8A. The extracted image Ie corresponds to an image obtained by extracting a group of pixels whose densities (signal values) are within a predetermined range (specific range a) from the cut image Ic.

The specific range a is determined such that a plurality of pixels P included in the specific range a have a uniform contrast according to the structure of the subject in the radiographic image. From another point of view, the specific range a is determined to be a range that does not include a signal value representing the contour of the structure included in the subject of the radiographic image (for example, the average value or the median of the signal values of the pixels of the contour).

Depending on the size of the region of interest ROI and the complexity of the structure of the subject, a bright portion corresponding to the contour of the structure (or a characteristic portion of the structure equivalent to the contour) may be included in the region of interest ROI. If the exposure index is calculated by using pixels including a portion equivalent to such a contour, it is difficult to appropriately evaluate the magnitude of noise. For this reason, the specific range a is determined so as not to include the signal value representing the contour of the structure. When the median or average value of the signal values in the density histogram H is set as a representative value b, signal values very close to the representative value b usually correspond to portions different from the contour of the structure. Therefore, by setting the value c when the specific range a is set to "b±c %" to be equal to or less than a predetermined upper limit value (specifically, "6(%)" or less), the contrast according to the structure of the subject in the specific range a can be made uniform. However, if the value c is too small, the number of extracted pixels is reduced to lower the stability of the exposure index as an index. Therefore, it is preferable that the value c is equal to or greater than a predetermined lower limit value (specifically, "1(%)" or more).

After extracting the plurality of pixels P, the controller 31 calculates the representative value (the average value in the present embodiment) and the standard deviation of the signal values of the plurality of extracted pixels P (step S34 in FIG. 5). The standard deviation is calculated by adding the square of the difference between the average value of the signal values of the plurality of pixels P and each signal value for each of the plurality of pixels P, dividing the obtained addition value by the number of plurality of pixels P, and taking the square root. Calculating the standard deviation corresponds to analyzing variations in the signal values of the plurality of pixels P extracted in step S33, and the standard deviation corresponds to the analysis result of the variations.

The representative value of the signal values of the plurality of pixels P calculated in step S34 is not limited to the average value, and may be a median, for example.

The controller 31 specifies the scattered ray content rate in the radiographic image (step S35). The scattered ray content rate tends to increase as the body thickness of the subject increases. Therefore, the scattered ray content rate can be estimated from the body thickness of the subject. The body thickness of the subject may be directly measured, or may be estimated by using various known methods. For example, since a histogram of signal values of a radiographic image tends to have a narrower width as the body thickness increases, the body thickness may be estimated from the histogram. Alternatively, since the BMI (body mass index), which is a value obtained by dividing the weight by the square of the height, has a correlation with the body thickness, the body thickness may be estimated from the BMI. The controller 31 specifies the scattered ray content rate based on the body thickness estimated or measured by these methods. The method for specifying the scattered ray content rate from the body thickness is not particularly limited, but for example, table data in which the body thickness and the scattered ray content rate are stored in association with each other may be referred to, or the scattered ray content rate may be calculated by using a function that returns the scattered ray content rate with the body thickness as an argument.

Then, the controller 31 calculates an exposure index by using the average value and the standard deviation calculated in step S34 and the scattered ray content rate specified in step S35 (step S36). In the present embodiment, assuming that the average value of the signal values of the plurality of pixels P is V, the scattered ray content rate in the radiographic image is R, the standard deviation is N, and the exposure index is I, the controller 31 calculates the exposure index I according to the following Equation (1).

$$I=(V(1-R))/N \quad (1)$$

The average value V of the signal values of the plurality of pixels P includes the influence of scattered rays scattered by the subject. Therefore, in Equation (1), the influence of scattered rays is removed by multiplying the average value V by (1−R) indicating the ratio of radiation excluding scattered rays to the dose of arrival. That is, (V(1−R)) in Equation (1) corresponds to a value obtained by subtracting the dose of scattered rays from the dose of arrival in the region of interest ROI, and corresponds to the magnitude of the signal (S in the SN ratio) in the region of interest ROI. The standard deviation N corresponds to the magnitude of noise (N in the SN ratio) in the region of interest ROI. Therefore, the exposure index I is a value corresponding to the SN ratio of the region of interest ROI. Since the region of interest ROI is a representative part of the radiographic image, it can be said that the exposure index I indicates the representative value of the SN ratio of the radiographic image.

Depending on the subject or imaging conditions, the exposure index I may be calculated according to the following Equation (2) or Equation (3).

$$I=((V(1-R))/N)^2 \quad (2)$$

$$I=(V(1-R))^2/N \quad (3)$$

The exposure index I in Equation (2) corresponds to the square of the SN ratio. In the exposure index I in Equation (2), a variance (the square of the standard deviation N) is used as the variations in the signal values of the plurality of pixels P extracted in step S33.

Assuming that S is the magnitude of the signal and N is the magnitude of the noise in the SN ratio, the exposure index I in Equation (3) corresponds to "$S^2/N$".

After calculating the exposure index, the controller 31 calculates a deviation index indicating the degree of deviation of the exposure index from the target value of the exposure index based on the calculated exposure index and the target value of the exposure index (step S37). The deviation index can be calculated by using, for example, the same method as the conventional calculation of the DI (deviation index) indicating the degree of deviation of the second exposure index (EI) from the target value. Specifically, the deviation index is calculated by substituting the calculated exposure index and the set target value into the following Equation (4).

$$\text{Deviation index}=10\ \text{Log}_{10}(\text{exposure index/target value of exposure index}) \quad (4)$$

When step S37 ends, the controller 31 ends the index calculation processing and returns to the processing at the time of imaging in FIG. 4.

In the above description, a plurality of pixels P are extracted based on one specific range a, and one exposure index is calculated. However, two or more exposure indices may be calculated based on one radiographic image. For example, a plurality of pixels Q having signal values within a specific range (second specific range) different from the specific range a may be further extracted from the density histogram H, a second exposure index may be calculated based on the signal values of the plurality of extracted pixels Q, and a representative exposure index (for example, an average value of the two exposure indices) may be calculated based on the obtained two exposure indices. In this manner, it is possible to further reduce the error of the exposure index caused by the inclusion of a structure in the region of interest ROI.

In the index calculation processing, a step of calculating a second exposure index (EI, which is a conventional exposure index) related to the dose reaching the radiation detector 2 based on the image data of the radiographic image may be included.

In this case, a step of calculating a second deviation index (conventionally used DI) indicating the degree of deviation of the second exposure index from the second target value based on the second exposure index and the second target value (conventionally used EIT (target exposure index)) of the second exposure index may be further included.

Returning to FIG. 4, when the index calculation processing of step S3 ends, the controller 31 determines whether or not the calculated exposure index is within the target range based on the target value of the exposure index set in step S1 (step S4). Specifically, it is determined whether or not the value of the deviation index is equal to or less than a predetermined value or whether or not the difference between the value of the exposure index and the target value is within a predetermined value.

When the step of calculating the second exposure index (EI) is included in the index calculation processing of step S3, it may also be determined in step S4 whether or not the second exposure index is within a second target range based on the second target value (EIT) of the second exposure index.

The controller 31 stores subject information, imaging conditions, the calculated exposure index and second exposure index, the specified scattered ray content rate, and the like when capturing the radiographic image in the database 41 for each imaging part, each subject's physique, each user, or each modality (step S5). Based on the data stored in the database 41, for example, an appropriate target value of the exposure index (and an appropriate second target value of the second exposure index) for each body thickness can be set (or adjusted). When updating the database 41 in step S5, the target value of the exposure index stored in the storage 33 of the console 3 may be updated according to the contents of the data in the database 41 after updating.

The controller 31 causes the notifier 34 to provide notification based on the calculated exposure index (step S6). Specifically, the notifier 34 notifies of at least one value of the calculated exposure index, the target value of the exposure index, and the calculated deviation index. With this notification, the user can recognize that the SN ratio of the radiographic image is low and the image quality is low, for example, when the deviation of the exposure index from the target value (deviation index) is large. Therefore, the user can re-capture a radiographic image after adjusting the imaging conditions to improve the image quality (for example, after making an adjustment to increase one or more of the tube current, tube voltage, and tube current-time product). The notification in this step may be performed only when the deviation of the exposure index from the target value is equal to or greater than a predetermined value or only when the deviation index is equal to or less than a predetermined value. Therefore, when the SN ratio of the radiographic image is equal to or less than a predetermined value, it is possible to prompt the user to adjust the imaging conditions and re-capture an image.

The notification by the notifier 34 may be screen display, light emission, sound, vibration, or a combination of two or more of these.

Figure 9:
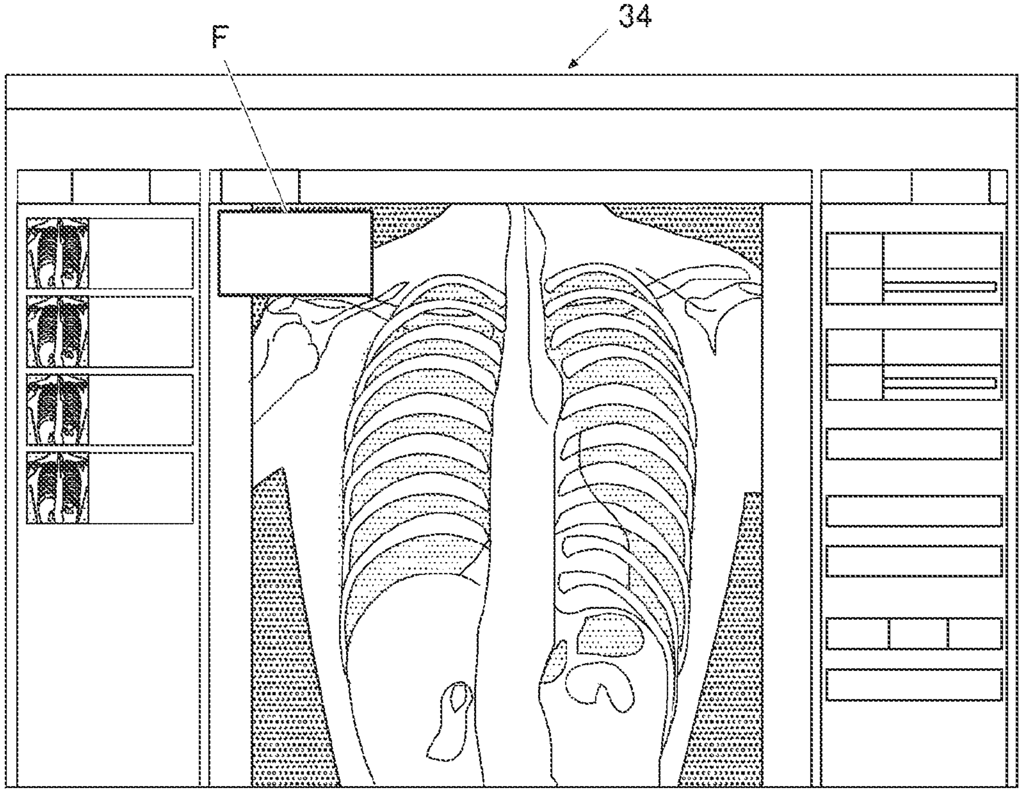
FIG. 9 is a diagram showing an example of an exposure index notification method.

When the notification is performed by screen display (when the notifier 34 is a display device), the display is performed in a region of the radiographic image where the subject is not shown (for example, a region indicated by the frame F in FIG. 9) or the like in the same manner as the conventionally used second exposure indices (EI, EIT, and DI). Therefore, the user can manage the dose in consideration of noise in the same operation method as for the conventional second exposure index and the like.

When the user is notified of the deviation index, the user can immediately grasp whether or not the image quality (SN ratio) of the radiographic image is sufficient based on the magnitude of the deviation index immediately after the end of imaging.

In addition, when the user is notified of the target value of the exposure index, the user can set an appropriate target value in consideration of a change in signal value or scattered ray content rate according to physique and a change in signal value or scattered ray content rate according to the presence or absence of grid or the presence or absence of scattered ray correction processing.

When the processing of calculating the second exposure index is included in the index calculation processing of step S3, the user may be notified of the calculated second exposure index together with the exposure index. In this manner, it becomes easier to understand the correspondence between the exposure index, the target value of the exposure index, and the deviation index according to the present embodiment and the second exposure index (EI), the target value of the second exposure index (EIT), and the deviation index (DI).

When it is determined in step S4 that the second exposure index is within the second target range and the exposure index is not within the target range, the user may be notified of the fact. In this manner, it is possible to find a radiographic image with insufficient image quality that has been overlooked by merely looking at the conventional second exposure index and prompt the user to re-capture an image.

When the degree of deviation between the deviation index of the exposure index and the second deviation index of the second exposure index is equal to or greater than a predetermined value, notification may be provided to prompt the user to change the second target value of the second exposure index.

When the appropriate target value of the exposure index based on the information stored in the database 41 in step S5 deviates from the current target value set in step S1 by a predetermined value or more, notification may be provided to prompt the user to change the current target value. This notification may be provided in step S1 to be executed next time.

When the exposure index stored in the database 41 is totaled for each predetermined period (for example, one month) and it is determined that the number of times the exposure index deviates from the target value by a predetermined value or more is equal to or greater than a predetermined number (frequent deviation) or that the deviation of the exposure index from the target value is equal to or greater than a predetermined value (large deviation), the user may be notified of the fact or an appropriate target value.

The controller 31 determines whether or not the radiographic image capturing has ended (step S7). When it is determined that the radiographic image capturing has not ended (the next radiographic image will be captured) ("NO" in step S7), the controller 31 proceeds to step S2. Alternatively, when the target value of the exposure index is updated when updating the database 41 in step S5, the process may proceed to step S1 instead of step S2 to set the target value of the exposure index again based on the latest data at that time.

When it is determined that the radiographic image capturing has ended ("YES" in step S7), the controller 31 ends the processing at the time of imaging.

First Modification Example

Next, a first modification example of the above embodiment will be described. This modification example is different from the above-described embodiment in that an image processing parameter is determined based on the calculated exposure index and image processing on a radiographic image is performed based on the image processing parameter. Hereinafter, differences from the above embodiment will be described, and explanations of contents common to the above embodiment will be omitted.

Figure 10:
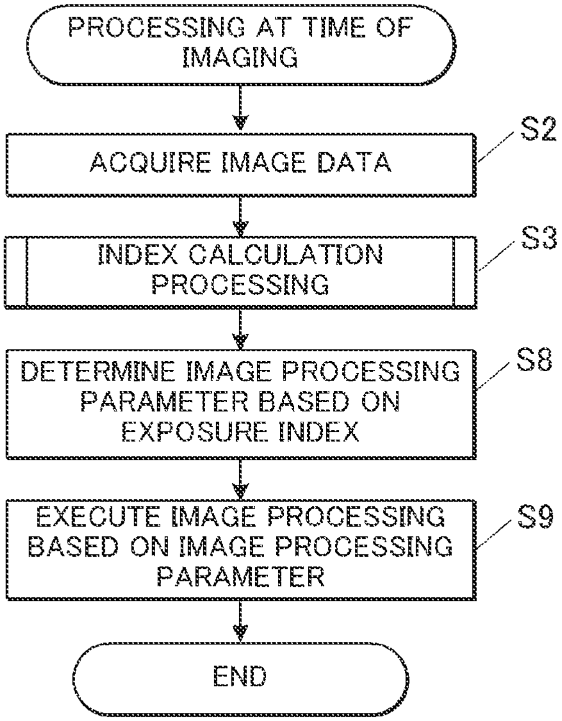
FIG. 10 is a flowchart showing the control procedure of processing at the time of imaging according to a first modification example.

FIG. 10 is a flowchart showing the control procedure of processing at the time of imaging according to the first modification example.

In the processing at the time of imaging shown in FIG. 10, steps S1 and S4 to S7 are removed from the processing at the time of imaging shown in FIG. 4, and steps S8 and S9 are added. When the processing at the time of imaging shown in FIG. 10 is started, the controller 31 acquires the image data of a radiographic image (step S2), and executes index calculation processing (step S3) as in the above embodiment.

After the exposure index is calculated by the index calculation processing, the controller 31 determines an image processing parameter based on the calculated exposure index (step S8), and executes predetermined image processing on the image data of the radiographic image based on the determined image processing parameter (step S9).

Examples of the image processing executed in step S9 include scattered ray correction processing for reducing the influence of scattered rays on the radiographic image. The scattered ray correction processing includes first processing for improving the contrast of the image by removing the signal amount of the scattered ray image equivalent to scattered rays from the original radiographic image. In the first processing, a signal amount equivalent to scattered rays to be removed from the original image is determined based on a first image processing parameter corresponding to the scattered ray content rate. In step S8 before step S9, the controller 31 determines the first image processing parameter used in the first processing based on the exposure index. Then, in subsequent step S9, the first processing is executed to remove the signal amount of the scattered ray image equivalent to scattered rays from the image data of the radiographic image based on the determined first image processing parameter.

In the scattered ray correction processing, second processing for reducing noise caused by scattered ray components to improve graininess may be performed after the first processing. In the first processing described above, while the low-frequency components of the scattered rays are removed, noise components having higher frequencies remain. As a result, graininess deteriorates. For this reason, it is preferable to reduce noise by suppressing graininess by further performing the second processing. In the second processing, processing for reducing noise with an intensity corresponding to a second image processing parameter indicating the magnitude of noise is executed. In step S8 before step S9, the controller 31 determines the second image processing parameter used in the second processing based on the exposure index. Then, in subsequent step S9, second processing for reducing noise is executed subsequent to the above-described first processing based on the determined second image processing parameter.

The image processing executed in step S9 is not limited to the scattered ray correction processing, and may be any image processing using an image processing parameter related to noise. In this case, in step S8, the image processing parameter used in the image processing may be determined in accordance with the image processing executed in step S9.

The flowchart of the processing at the time of imaging in this modification example is not limited to that shown in FIG. 10. For example, processing for determining the image processing parameter of this modification example (step S8) and processing for executing image processing based on the image processing parameter (step S9) may be combined with the processing at the time of imaging of the above embodiment shown in FIG. 4.

Second Modification Example

Next, a second modification example of the above embodiment will be described. This modification example is different from the above-described embodiment in that an exposure index related to noise is calculated based on the image data of one radiographic image in continuous radiographic image capturing and the imaging conditions for the remaining imaging in the continuous imaging are adjusted based on the calculated exposure index. Hereinafter, differences from the above embodiment will be described, and explanations of contents common to the above embodiment will be omitted. The second modification example may be combined with the first modification example.

Figure 11:
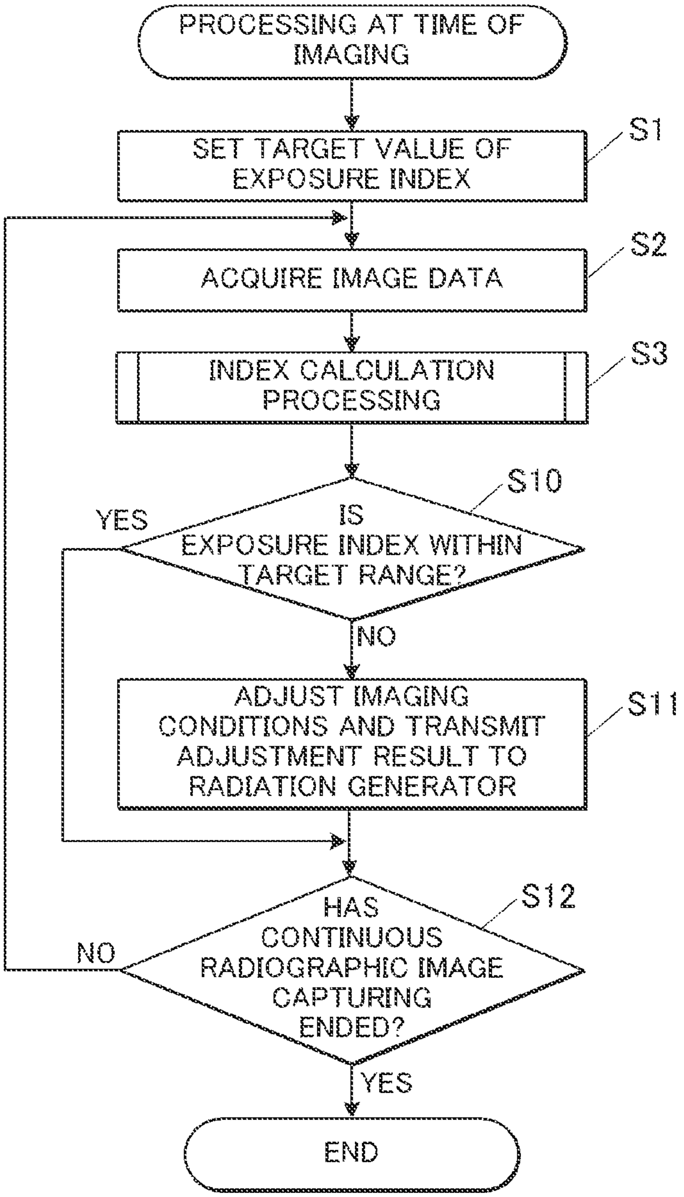
FIG. 11 is a flowchart showing the control procedure of processing at the time of imaging according to a second modification example.

FIG. 11 is a flowchart showing the control procedure of processing at the time of imaging according to the second modification example.

In the processing at the time of imaging shown in FIG. 11, steps S4 to S7 are removed from the processing at the time of imaging shown in FIG. 4, and steps S10 to S12 are added. The processing at the time of imaging according to this modification example is started when the radiographic imaging system 100 performs continuous radiographic image capturing. In the continuous radiographic image capturing, for example, irradiation and radiographic image generation are repeatedly performed at a predetermined frame rate of 3 to 60 fps to generate a moving radiographic image. With the moving radiographic image, the internal structure or state of the subject can be seen through in real time. The radiographic imaging system 100 capable of performing continuous imaging is also called a fluoroscope, an X-ray TV, and the like.

When the processing at the time of imaging shown in FIG. 11 is started, the controller 31 sets the target value of the exposure index (step S1). After the target value is set, continuous radiographic image capturing by the radiation generator 1 and the radiation detector 2 is started. The controller 31 acquires image data of a radiographic image generated first (step S2), and executes index calculation processing in the same manner as in the embodiment described above (step S3).

When the exposure index is calculated by the index calculation processing, the controller 31 determines whether or not the calculated exposure index is within the target range based on the target value of the exposure index set in step S1 (step S10). Specifically, it is determined whether or not the value of the deviation index is equal to or less than a predetermined value or whether or not the difference between the value of the exposure index and the target value is within a predetermined value.

When it is determined that the exposure index is not within the target range ("NO" in step S10), the controller 31 adjusts (determines) the imaging conditions for radiographic image capturing to be executed thereafter, and transmits the adjustment result to the radiation generator 1 to change the operation setting (step S11). When the exposure index is smaller than the target range (the SN ratio is insufficient), the controller 31 adjusts the imaging conditions such that the SN ratio increases. For example, the controller 31 makes an adjustment to increase at least one of the tube voltage (kV), the tube current (mA), and the tube current-time product (mAs). In addition, when the exposure index is larger than the target range (the SN ratio is larger than necessary), the controller 31 adjusts the imaging conditions such that the SN ratio decreases. For example, the controller 31 makes an adjustment to reduce at least one of the tube voltage, the tube current, and the tube current-time product.

The items of the imaging conditions to be adjusted are not limited to the tube voltage, the tube current, and the tube current-time product. The imaging conditions are not limited to the conditions related to the operation of the radiation generator 1, and may include conditions related to the operation of the radiation detector 2 (for example, a frame rate for generating a radiographic image). In this case, the controller 31 transmits the adjustment result of the imaging conditions to each device to be adjusted to change the operation setting.

After the end of step S11 or when it is determined in step S10 that the exposure index is within the target range ("YES" in step S10), the controller 31 determines whether or not the continuous radiographic image capturing has ended (step S12). When it is determined that the continuous radiographic image capturing has not ended ("NO" in step S12), the controller 31 returns to step S2. Thereafter, for the image data of the next radiographic image in the continuous imaging, the calculation of the exposure index (step S3), the determination as to whether or not the exposure index is within the target range (step S10), and the adjustment of the imaging conditions (step S11) are executed.

The series of processes of steps S2, S3, S10, and S11 may not be executed for all radiographic images in continuous imaging, and may be executed for some radiographic images at a predetermined frequency, for example.

Alternatively, the series of processes of steps S2, S3, S10, and S11 may be executed only for the radiographic image generated first, and subsequent radiographic images may be generated under the same imaging conditions. In this case, when "NO" in step S12, step S12 may be executed again.

When it is determined in step S12 that the continuous radiographic image capturing has ended ("YES" in step S12), the controller 31 ends the processing at the time of capturing.

Third Modification Example

The processing related to the calculation of the exposure index in the above embodiment includes processing for extracting a plurality of pixels P from the density histogram H and processing with a small computational load, such as calculating the average value and standard deviation of the signal values of a plurality of extracted pixels P, but does not include processing with a large computational load, such as spatial frequency analysis including Fourier transform processing. Therefore, even a computer with relatively low computing power can execute the index calculation processing including the calculation of the exposure index (FIG. 5) or the processing at the time of imaging (FIG. 4).

For this reason, for example, the detector controller 21 of the radiation detector 2 may execute at least the processing for calculating the exposure index of the processing at the time of imaging and the index calculation processing executed by the controller 31 of the console 3 in the above embodiment. In this case, the "image processing apparatus" is formed by the components (the detector controller 21, the communicator 22, the storage 23, and the operation interface 25) of the radiation detector 2 shown in FIG. 2 excluding the detection sensor 24. According to this configuration, for example, it is possible to calculate the exposure index in the portable (cassette type) radiation detector 2.

At least the processing for calculating the exposure index of the processing at the time of imaging and the index calculation processing executed by the controller 31 of the console 3 in the above embodiment may be executed by another device (for example, the radiation generator 1) of the radiographic imaging system 100 or may be executed by another system connected to the radiographic imaging system 100. In this case, the device or system that executes the processing for calculating the exposure index corresponds to the "image processing apparatus".

The third modification example may be combined with the first modification example and/or the second modification example.

Fourth Modification Example

Next, a fourth modification example of the above embodiment will be described. This modification example is different from the above embodiment in the method of creating the density histogram H. Hereinafter, differences from the above embodiment will be described, and explanations of contents common to the above embodiment will be omitted. The fourth modification example may be combined with some or all of the first to third modification examples.

The region of interest ROI exemplified in FIG. 6 of the above embodiment includes only a subject region corresponding to the subject, and does not include a transparent region. Here, the transparent region is a region where the radiation is directly incident without passing through the subject (more specifically, a region where the radiation directly reaches the pixels of the detection sensor 24 without passing through the subject).

However, when the subject has a complicated structure, such as a radiographic image of a finger, it is difficult to set the region of interest ROI so as not to include the transparent region.

Figure 12:
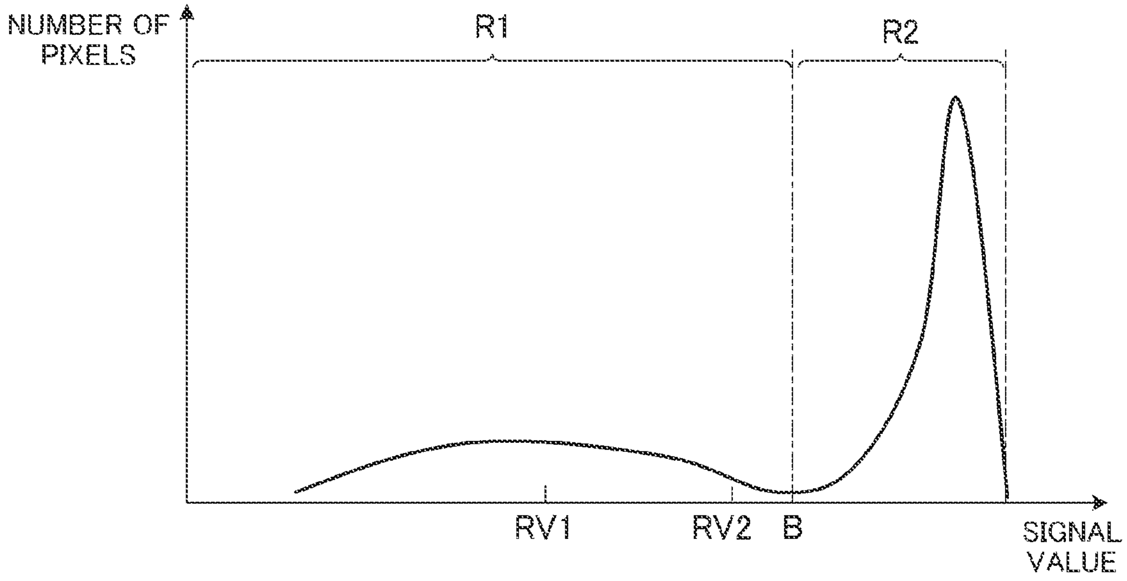
FIG. 12 is a diagram showing an example of a density histogram of a region of interest including a transparent region.

FIG. 12 is a diagram showing an example of the density histogram H of the region of interest ROI including a transparent region R2.

In the transparent region R2, the amount of radiation incident on the pixels of the detection sensor 24 is larger than that in a subject region R1. For this reason, the signal value of each pixel in the transparent region R2 is larger than that in the subject region R1. Therefore, assuming that the boundary value between the signal value of the subject region R1 and the signal value of the transparent region R2 is a "boundary value B", as shown in FIG. 12, in the density histogram H, a region where the signal value is larger than the boundary value B corresponds to the transparent region R2, and a region where the signal value is smaller than the boundary value B corresponds to the subject region R1.

When the region of interest ROI includes the transparent region R2, the representative value (here, the median) of the signal values derived from the density histogram H created from the entire region of interest ROI is a representative value RV2 in FIG. 12, for example. This representative value RV2 is larger than a representative value RV1 in a case where it is assumed that the representative value is derived only for the subject region R1, due to the influence of the pixels in the transparent region R2 having a large signal value. Therefore, the specific range a set so that the representative value RV2 is centered in the region of interest ROI becomes inappropriate, and the analysis result (average value or standard deviation) of the signal values of the pixels belonging to the specific range a also becomes inappropriate.

Therefore, in this modification example, the density histogram H is created based on the signal values of the pixels of the subject region R1, which is a region excluding the transparent region R2 from the region of interest ROI. Specifically, first, the density histogram H shown in FIG. 12 is created based on the entire region of interest ROI including the transparent region R2, and the boundary value B of the signal values between the subject region R1 and the transparent region R2 is specified. Then, the pixels of the subject region R1, excluding the pixels of the transparent region R2 where the signal value is larger than the boundary value B, are extracted. Then, the density histogram H is created again based on the signal values of the extracted pixels.

Here, the boundary value B can be, for example, a signal value that gives a minimum value (bottom) between the subject region R1 and the transparent region R2 in the density histogram H shown in FIG. 12. In this method, a small number of pixels in the transparent region R2 may be included in a region where the signal value is smaller than the boundary value B. However, since the number of pixels is very small compared with the number of pixels in the subject region R1, there is no problem with the analysis.

FIG. 13 is a flowchart showing the control procedure of index calculation processing according to the fourth modification example.

The flowchart of FIG. 13 is obtained by adding step S38 before step S32 in the flowchart of FIG. 5 and changing step S32 to step S32*a*. In the index calculation processing of this modification example, after setting the region of interest ROI in step S31, the controller 31 extracts pixels of the subject region R1, which is a region excluding the transparent region R2 from the region of interest ROI, by using the method described above (step S38). Then, the controller 31 creates the density histogram H based on the signal values of the pixels extracted from the region of interest ROI (step S32*a*). Since the subsequent steps S33 to S37 are the same as in FIG. 5, explanations thereof will be omitted. By using this index calculation processing, even when the region of interest ROI includes the transparent region R2, the specific range a can be appropriately set in step S33. In addition, in step S34, it is possible to calculate an average value (representative value) that more appropriately reflects the information of the subject.

Fifth Modification Example

Next, a fifth modification example of the above embodiment will be described. This modification example is different from the above embodiment in that filtering processing for reducing low-frequency signals is performed before analyzing variations in signal values of a plurality of pixels belonging to the specific range a. Hereinafter, differences from the above embodiment will be described, and explanations of contents common to the above embodiment will be omitted. The fifth modification example may be combined with some or all of the first to fourth modification examples.

The region of interest ROI exemplified in FIG. 6 of the above embodiment hardly includes the shading due to the structure of the subject such as the contour of the bone. However, in cases such as when the structure of the subject is complicated, it is difficult to set the region of interest ROI so as not to include the shading due to the structure of the subject. In such a case, if the variations in signal values of a plurality of pixels belonging to the specific range a are analyzed (for example, the standard deviation is calculated) by using the region of interest ROI as it is, variations in signal values due to the structure of the subject are reflected.

Therefore, in this modification example, filtering processing for reducing low-frequency signals is performed in the region of interest ROI or an image region of a predetermined size including the region of interest ROI before analyzing the variations in signal values. Here, the frequency range of low-frequency signals to be reduced is a frequency range on the lower frequency side than the frequency of noise that does not depend on the structure of the subject, including a frequency corresponding to the structure of the subject. Although the specific method of filtering processing is not particularly limited, for example, a method of performing image filtering (spatial filtering) by convolution integral for the image data of the region of interest ROI or an image region of a predetermined size including the region of interest ROI may be used. In addition, a method of performing frequency filtering by Fourier transform processing may be used when the controller 31 has sufficient processing capacity.

In this modification example, step S34 in the flowchart of the index calculation processing shown in FIG. (or FIG. 13 when this modification example is combined with the fourth modification example) is changed as follows.

Figure 14:
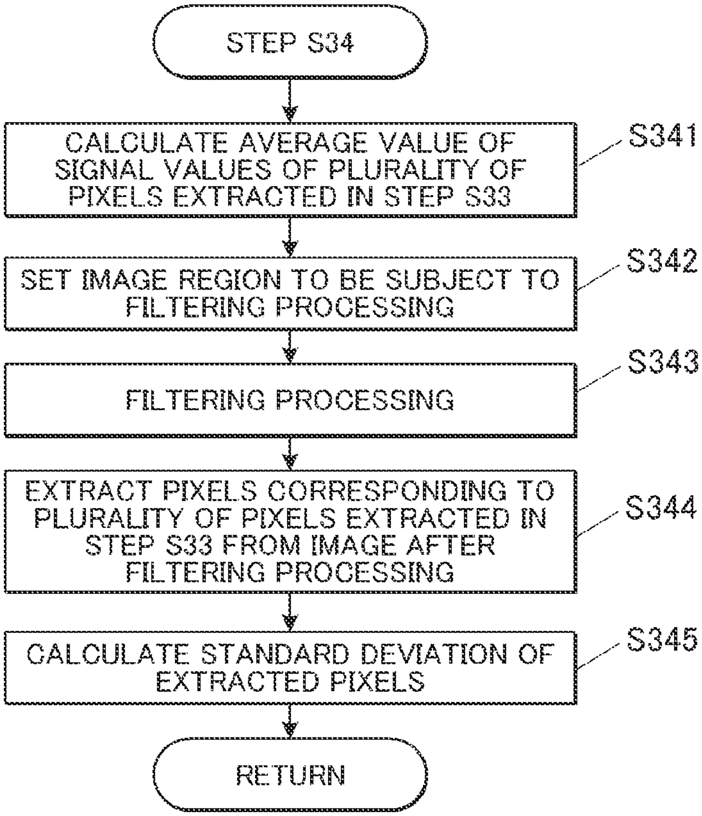
FIG. 14 is a flowchart showing the control procedure of step S34 in index calculation processing according to a fifth modification example.

FIG. 14 is a flowchart showing the control procedure of step S34 in index calculation processing according to a fifth modification example. In the flowchart of FIG. 14, step S341 corresponds to processing for calculating the average value of the signal values of a plurality of pixels belonging to the specific range a, and steps S342 to S345 correspond to processing for analyzing variations in signal values of the plurality of pixels (processing for calculating the standard deviation).

When step S34 is started, the controller 31 calculates the average value of the signal values of the plurality of pixels belonging to the specific range a extracted in step S33 (step S341).

Then, the controller 31 sets an image region to be subject to filtering processing (step S342). Here, the controller 31 sets the region of interest ROI itself or an image region of a predetermined size including the region of interest ROI as the image region to be subject to filtering processing. Thereafter, the controller 31 performs the above-described filtering processing for reducing low-frequency signals on the set image region (step S343).

Then, the controller 31 extracts pixels corresponding to the plurality of pixels belonging to the specific range a extracted in step S33 from the image after the filtering processing (step S344). Then, the controller 31 calculates the standard deviation of the pixels extracted in step S344 (step S345).

When step S345 ends, the controller 31 ends the entire step S34 and proceeds to step S35 of the index calculation processing. Since the subsequent steps S35 to S37 are the same as in FIG. 5 (or FIG. 13), explanations thereof will be omitted. By using this method, variations in signal values due to the structure of the subject are suppressed. As a result, it is possible to more appropriately calculate the standard deviation of the signal values of a plurality of pixels belonging to the specific range a (analyze the variations).

Effects

As described above, the console 3 as an image processing apparatus according to the present embodiment includes the controller 31 (calculator) that calculates the exposure index related to the noise of the radiographic image based on the image data of the radiographic image. The controller 31 creates the density histogram H of the region of interest ROI set in a part of the radiographic image, extracts a plurality of pixels P having signal values within the specific range a from the created density histogram H, analyzes variations in the signal values of the plurality of extracted pixels P, and calculates the exposure index based on the analysis result of the variations.

According to this, it is possible to calculate the exposure index by processing with a small processing load, such as processing for extracting a plurality of pixels P having signal values within the specific range a from the density histogram H or processing for analyzing variations in the pixel values of the plurality of extracted pixels P, and the calculation of the exposure index does not require processing with a large computational load, such as spatial frequency analysis including Fourier transform processing. Therefore, an appropriate exposure index can be calculated by simple processing with a small computational load. As a result, it is possible to reduce the processing load on the console 3. The exposure index can also be calculated by an image processing apparatus with low processing power (for example, an information processing apparatus mounted on a medical care vehicle or a compact and portable device such as the radiation detector 2). In general, performing a Fourier transform using N pieces of data requires the amount of calculation on the order of $N^2$, whereas analyzing variations (for example, calculating the standard deviation) in N pieces of data as in the present embodiment requires the amount of calculation on the order of N. Therefore, according to the configuration of the present embodiment, the larger the size of the radiographic image, the more effectively the computational load can be reduced. In addition, since the exposure index can be calculated in a short time, it is possible to adjust subsequent imaging conditions in real time based on the calculated exposure index.

In addition, when setting the region of interest ROI, even if a special adjustment to make uniform the contrast according to the subject's structure (contour, surface unevenness, or the like) is not performed, the influence of the contrast can be reduced by the processing for analyzing the density histogram H and the processing for extracting the pixel P within the specific range a.

In addition, by referring to the exposure index related to noise, it is possible to determine not only the amount of radiation reaching the radiation detector 2 but also whether or not a radiographic image with a desired image quality (SN ratio) has been obtained. Therefore, it is possible to prompt the user to emit radiation with the optimum dose with which a radiographic image with a desired image quality can be captured. As a result, it is possible to suppress the occurrence of problems such as loss of diagnostic value due to insufficient dose and increased radiation exposure due to excessive dose.

In addition, in the fourth modification example, the controller 31 (calculator) creates the density histogram H based on the signal values of the pixels of the subject region R1, which is a region excluding the transparent region R2 where the radiation is directly incident without passing through the subject from the region of interest ROI. Therefore, even when the region of interest ROI includes the transparent region R2, the specific range a can be appropriately set. In addition, for the signal values of the pixels belonging to the specific range a, it is possible to perform analysis (calculation of the average value) that more appropriately reflects the information of the subject. As a result, the information of the subject region R1 from which the transparent region R2 has been removed can be more appropriately reflected in the magnitude (S in the SN ratio) of the signal in the exposure index, thereby improving the accuracy of the exposure index.

The specific range a is determined such that a plurality of pixels P have a uniform contrast according to the structure of the subject in the radiographic image. Therefore, it is possible to suppress the influence of the contrast of the structure (for example, bone) of the subject and reduce the exposure index error caused by the contrast of the structure.

The controller 31 (calculator) calculates the exposure index further based on the representative value of the signal values of the plurality of pixels P. Therefore, the exposure index can be calculated by using an easy analysis method. The exposure index can include information regarding the magnitude of the signal of the radiographic image.

The controller 31 (calculator) specifies the scattered ray content rate in the radiographic image, and calculates the exposure index further based on the specified scattered ray content rate. Therefore, it is possible to calculate the exposure index indicating the SN ratio in consideration of the magnitude of noise caused by scattered rays.

The representative value is the average value of the signal values of the plurality of pixels P, and the variation analysis result includes the standard deviation of the signal values of the plurality of pixels P. Assuming that V is the average value, N is the standard deviation, S is the scattered ray content rate, and I is the exposure index, the controller 31 (calculator) calculates the exposure index according to the following Equation (1).

$$I=(V(1-S))/N \quad (1)$$

Therefore, by using the simple analysis method, it is possible to calculate an appropriate exposure index indicating the SN ratio in consideration of the magnitude of noise caused by scattered rays.

The controller 31 (calculator) may calculate the exposure index according to the following Equation (2).

$$I=((V(1-S))/N)^2 \quad (2)$$

Therefore, by using the simple analysis method, it is possible to calculate an appropriate exposure index indicating the square of the SN ratio in consideration of the magnitude of noise caused by scattered rays.

In addition, in the fifth modification example, the controller 31 (calculator) performs filtering processing for reducing low-frequency signals in the region of interest ROI or an image region including the region of interest ROI, and analyzes variations in signal values of the plurality of pixels after the filtering processing. Therefore, since variations in signal values due to the structure of the subject are suppressed, it is possible to more appropriately calculate the standard deviation of the signal values of a plurality of pixels belonging to the specific range a. That is, it is possible to more appropriately analyze variations in signal values of a plurality of pixels. In other words, it is possible to reduce the error in the analysis result caused by the contrast of the structure of the subject. As a result, it is possible to further improve the accuracy of the exposure index.

In the first modification example, the controller 31 functions as an image processor that performs image processing on the image data of a radiographic image. In addition, the controller 31 (image processor) determines an image processing parameter based on the calculated exposure index, and performs image processing based on the image processing parameter. Therefore, the image processing parameter can be individually optimized according to the body type of the subject (patient) or the imaging conditions. As a result, it is possible to perform more appropriate image processing according to the body type of the subject or the imaging conditions.

In the second modification example, when continuously capturing radiographic images of the subject, the controller 31 (calculator) calculates an exposure index based on the image data of one radiographic image in the continuous imaging. The controller 31 functions as a determinator that determines, based on the calculated exposure index, imaging conditions related to imaging after the calculation of the exposure index in the continuous imaging. Therefore, the imaging conditions (tube voltage (kV), tube current (mA), tube current-time product (mAs), and the like) can be optimized in real time and at high speed according to the image quality that changes moment by moment during imaging due to changes in the subject's (patient's) posture, administration of contrast media, and the like.

The console 3 includes the notifier 34 that provides notification based on the calculated exposure index. Therefore, the user can recognize not only the amount of radiation reaching the radiation detector 2 but also whether or not a radiographic image with a desired image quality (SN ratio) has been obtained. Therefore, it is possible to prompt the user to emit radiation with the optimum dose with which a radiographic image with a desired image quality can be captured. As a result, it is possible to suppress the occurrence of problems such as loss of diagnostic value due to insufficient dose and increased radiation exposure due to excessive dose.

The controller 31 (calculator) calculates a deviation index indicating the degree of deviation of the exposure index from the target value of the exposure index based on the calculated exposure index and the target value of the exposure index, and the notifier 34 provides notification based on the calculated deviation index. Therefore, the user can easily recognize whether or not the image quality (SN ratio) of the radiographic image is sufficient.

The radiation detector 2 according to the third modification example includes the detector controller 21, the communicator 22, the storage 23, and the operation interface 25 as the image processing apparatus described above and the detection sensor 24 that detects radiation and performs conversion into an electrical signal. The detector controller 21 functions as image data generator that generates image data of a radiographic image based on the signal value of the electrical signal output from the detection sensor 24. Therefore, for example, it is possible to calculate the exposure index in the portable (cassette type) radiation detector 2.

The program 331 according to the present embodiment causes the controller 31 as a computer to function as calculator that calculates an exposure index related to noise in a radiographic image based on the image data of the radiographic image. The calculator creates the density histogram H of the region of interest ROI set in the entire radiographic image or a part of the radiographic image, extracts a plurality of pixels P having signal values within the specific range a from the created density histogram H, analyzes variations in the signal values of the plurality of extracted pixels P, and calculates the exposure index based on the analysis result of the variations. Therefore, an appropriate exposure index can be calculated by simple processing with a small computational load.

Others

The present invention is not limited to the embodiment and its modification examples described above, and various modifications can be made.

For example, in the above embodiment, the standard deviation (N) and the variance ($N^2$) are exemplified as values (analysis results of variations) indicating variations in the signal values of a plurality of pixels P extracted from the density histogram H. However, any value can be used as long as the value indicates variations in the signal values of a plurality of pixels P. For example, an average deviation (a value obtained by averaging deviations of the signal values of pixels from the average value), an unbiased variance, a quartile deviation, and the like may be used.

Any exposure index having correlation with at least the magnitude of noise in a radiographic image may be used, and the exposure index is not limited to being calculated by the Equations (1) to (3) exemplified in the above embodiment.

For example, adjustment according to the scattered ray content rate (R) may not be performed. That is, instead of "$V(1-R)$" in Equations (1) to (3), the average value "V" may be simply used. For example, since there are few scattered rays in parts other than the trunk such as hands or feet, a highly reliable exposure index may be obtained even if the adjustment according to the scattered ray content rate is not performed.

The analysis result (standard deviation (N), variance ($N^2$), and the like) of the variations in the signal values of the plurality of pixels P extracted from the density histogram H may be used as an exposure index as it is. In this case, the conventional second exposure index (EI) may be used as an index related to the magnitude of the signal of the radiographic image, and the exposure index and the second exposure index may be combined to evaluate the radiographic image.

In the above embodiment, a part of the radiographic image is used as the region of interest ROI. However, the entire radiographic image may be used as the region of interest ROI.

The present invention can be applied to various types of radiographic imaging. For example, the present invention may be applied to the analysis of the first imaging in a method (for example, ScoutRAD) in which imaging and analysis are performed with a low dose for the first time to determine the imaging conditions and immediately after that, imaging is performed with the actual dose. The present invention may also be applied to radiographic imaging using various methods, such as dual energy X-ray absorptiometry (DXA) and dual energy subtraction (DES).

The exposure index may be calculated by the method of the present invention for a three-dimensional (3D) radiographic image without being limited to a two-dimensional (2D) radiographic image.

Radiographic images are not limited to medical images used for diagnosis of people, and subjects of radiographic images are not limited to living organisms such as humans. For example, objects other than living organisms, such as goods or structures, may be used as subjects.

Although embodiments of the present invention have been described and illustrated in detail, the disclosed embodiments are made for purposes of illustration and example only and not limitation. The scope of the present invention should be interpreted by terms of the appended claims.

The invention claimed is:

1. An image processing apparatus, comprising:
a first hardware processor that calculates an exposure index related to noise of a radiographic image based on image data of the radiographic image,
wherein the first hardware processor creates a density histogram of a region of interest set in the entire radiographic image or a part of the radiographic image, extracts a plurality of pixels having signal values within a specific range from the created density histogram, analyzes variations in the signal values of the plurality of pixels, an analysis result of the variations including a standard deviation of the signal values of the plurality of pixels, and assuming that V is an average value of the signal values of the plurality of pixels, N is the standard deviation, R is the scattered ray content rate, and I is the exposure index, calculates the exposure index based on the standard deviation of the signal values of the plurality of pixels according to first Equation, I=(V(1−R)/N, or second Equation, $I=((V(1-R))/N)^2$.

2. The image processing apparatus according to claim 1, wherein the first hardware processor creates the density histogram based on signal values of pixels in a subject region, which is a region excluding a transparent region where radiation is directly incident without passing through the subject from the region of interest.

3. The image processing apparatus according to claim 1, wherein the specific range is determined such that the plurality of pixels have a uniform contrast according to a structure of a subject in the radiographic image.

4. The image processing apparatus according to claim 1, wherein the first hardware processor calculates the exposure index further based on a representative value of the signal values of the plurality of pixels.

5. The image processing apparatus according to claim 4, wherein the first hardware processor specifies a scattered ray content rate in the radiographic image and calculates the exposure index further based on the specified scattered ray content rate.

6. The image processing apparatus according to claim 5, wherein the first hardware processor calculates the exposure index according to the first Equation, I=(V(1−R))/N.

7. The image processing apparatus according to claim 5, wherein the first hardware processor calculates the exposure index according to the second Equation, $I=((V(1-R))/N)^2$.

8. The image processing apparatus according to claim 1, wherein the first hardware processor performs filtering processing for reducing low-frequency signals in the region of interest or an image region including the region of interest, and analyzes variations in signal values of the plurality of pixels after the filtering processing.

9. The image processing apparatus according to claim 1, wherein the first hardware processor determines an image processing parameter based on the calculated exposure index for the image data of the radiographic image and performs image processing based on the image processing parameter.

10. The image processing apparatus according to claim 1, wherein, when continuously capturing radiographic images of a subject, the first hardware processor calculates the exposure index based on image data of one of the radiographic images in the continuous imaging, and
the first hardware processor determines, based on the calculated exposure index, imaging conditions related to imaging after calculation of the exposure index in the continuous imaging.

11. The image processing apparatus according to claim 1, further comprising:
a notifier that provides notification based on the exposure index calculated by the first hardware processor.

12. The image processing apparatus according to claim 11,
wherein the first hardware processor calculates a deviation index indicating a degree of deviation of the exposure index from a target value of the exposure index based on the calculated exposure index and the target value of the exposure index, and
the notifier provides notification based on the deviation index calculated by the first hardware processor.

13. A radiation detector, comprising:
the image processing apparatus according to claim 1;
a detection sensor that detects radiation and performs conversion into an electrical signal; and
a second hardware processor that generates the image data of the radiographic image based on a signal value of the electrical signal output from the detection sensor.

14. A non-transitory recording medium storing a computer readable program causing a computer to execute:
calculating an exposure index related to noise of a radiographic image based on image data of the radiographic image,
wherein, in the calculation, a density histogram of a region of interest set in the entire radiographic image or a part of the radiographic image is created, a plurality of pixels having signal values within a specific range are extracted from the created density histogram, variations in the signal values of the plurality of pixels are analyzed, an analysis result of the variations including a standard deviation of the signal values of the plurality of pixels, and assuming that V is an average value of the signal values of the plurality of pixels, N is the standard deviation, R is the scattered ray content rate, and I is the exposure index, the exposure index is calculated based on the standard deviation of the signal values of the plurality of pixels according to first Equation, I=(V(1−R)/N, or second Equation, $I=((V(1-R))/N)^2$.

* * * * *